United States Patent [19]

Esanu

[11] Patent Number: 4,681,888
[45] Date of Patent: Jul. 21, 1987

[54] THIENOPYRIDINE DERIVATIVES AND ANTI-THROMBOTIC COMPOSITIONS CONTAINING THE SAME

[75] Inventor: Andre Esanu, Paris, France

[73] Assignee: Societe de Conseils de Recherches et d'Applications Scientifiques, Paris, France

[21] Appl. No.: 894,780

[22] Filed: Aug. 8, 1986

Related U.S. Application Data

[63] Continuation-in-part of Ser. No. 792,484, Oct. 29, 1985, abandoned.

[30] Foreign Application Priority Data

Nov. 16, 1984 [GB] United Kingdom ............... 8429087

[51] Int. Cl.$^4$ .................... A61K 31/44; C07D 495/04
[52] U.S. Cl. .................................... 514/301; 546/114
[58] Field of Search ..................... 546/114; 514/301

[56] References Cited

U.S. PATENT DOCUMENTS 4,529,596 7/1985 Aubert et al. ................. 546/114

Primary Examiner—John M. Ford
Assistant Examiner—Bernard L. Dentz
Attorney, Agent, or Firm—Lucas & Just

[57] ABSTRACT

This invention relates to new derivatives of 5-(ω-phenethylamino-alkyl)-4,5,6,7-tetrahydro-thieno-(3,2-c)-pyridine of the formula

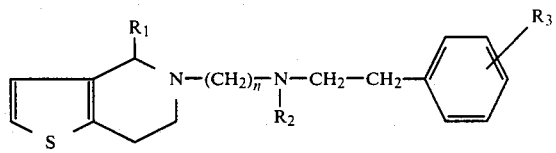

wherein n is an integer of from 2 to 5, $R_1$ represents a hydrogen atom or a 3,4-dimethoxyphenyl group, $R_2$ represents a hydrogen atom, an alkyl group having up to 4 carbon atoms or a 4-cyano-4-(3,4-dimethoxyphenyl)-5-methylhexyl group and $R_3$ represents two or three methoxy groups, to therapeutically acceptable salts thereof, to a process for the preparation of these derivatives comprising condensing a 5-(ω-chloroalkyl)-4,5,6,7-tetrahydro-thieno-(3,2-c)-pyridine with the appropriate phenethyl derivative at from 90° to 130° C. under nitrogen circulation and to therapeutic compositions containing said compounds.

2 Claims, No Drawings

THIENOPYRIDINE DERIVATIVES AND ANTI-THROMBOTIC COMPOSITIONS CONTAINING THE SAME

This application is a continuation-in-part of application Ser. No. 792,484 filed Oct. 29, 1985, now abandoned.

The invention relates to thienopyridine derivatives, to a process for their preparation and to therapeutic compositions containing them.

The invention provides derivatives of 5-(ω-phenethylamino-alkyl)-4,5,6,7-tetrahydro-thieno-(3,2-c)-pyridine of the general formula I

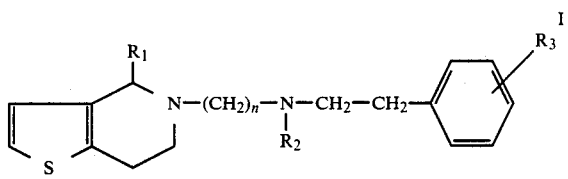

wherein n is an integer of from 2 to 5, $R_1$ represents a hydrogen atom or a 3,4-dimethoxyphenyl group, $R_2$ represents a hydrogen atom, an alkyl group having up to 4 carbon atoms or a 4-cyano-4-(3,4-dimethoxyphenyl)-5-methylhexyl group and $R_3$ represents two or three methoxy groups; and further provides therapeutically acceptable salts thereof.

These compounds are particularly interesting as anti-thrombotic agents with a complementary calcium antagonist activity.

The invention also provides a process for the preparation of the derivatives of the general formula I, the process comprising condensing a 5-(ω-chloroalkyl)-4,5,6,7-tetrahydro-thieno-(3,2-c)-pyridine of the general formula II

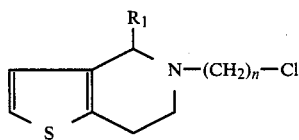

wherein n and $R_1$ are as above defined with a phenethylamine derivative of the general formula III

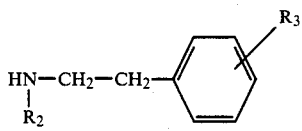

wherein $R_2$ and $R_3$ are as above defined at from 90° to 130° C. under nitrogen circulation.

The starting compound of the general formula II may be obtained by condensing the corresponding 5-unsubstituted thienopyridine with an ω-chloroalkyl bromide. The starting compound of the general formula III may be obtained, when $R_2$ does not represent a hydrogen atom, by condensation of $R_2Cl$ with the corresponding phenethylamine.

The invention further provides a therapeutic composition containing a compound of the general formula I or a therapeutically acceptable salt thereof in admixture with a therapeutically acceptable diluent or carrier.

The invention is illustrated by the following examples.

EXAMPLE 1

5-[N-(3,4-dimethoxyphenethyl)-2-aminoethyl]-4,5,6,7-tetrahydro-thieno-(3,2-c)-pyridine n=2, $R_1=R_2=H$, $R_3=3,4$-dimethoxy Into a two liter reactor, fitted with an oil-bath and stirring means and under nitrogen circulation, were poured 201.5 g (1 mol) of 5-(2-chloroethyl)-4,5,6,7-tetrahydro-thieno-(3,2-c)-pyridine and slowly, under stirring, 181 g (1 mol) of 3,4-dimethoxyphenethylamine. The reacting mixture was warmed at 110° C. under stirring for two hours. The oily mixture obtained was cooled to about 70°–80° C. and then poured into icy water; after separation, washing, extraction with diethyl ether and drying, the residue was dissolved in a mixture of petroleum ether and isopropyl ether (50/50 by volume) and passed through a silica gel column. Elution was with acetone. The fraction containing the desired compound was evaporated to dryness, treated with diethyl ether and finally with acetone. Yield 163 g (47%) of a white crystalline powder soluble in water, melting at 260° C. (Tottoli) with decomposition, the analysis and NMR of which showed a good correspondence with the formula $C_{19}H_{26}N_2O_2S$.

EXAMPLE 2

5-[N-(3,4-dimethoxyphenethyl)-N-methyl-2-aminoethyl]-4,5,6,7-tetrahydro-thieno-(3,2-c)-pyridine n=2, $R_1=H$, $R_2=CH_3$, $R_3=3,4$-dimethoxy Example 1 was repeated, but using N-methyl-3,4-dimethoxyphenethylamine instead of 3,4-dimethoxyphenethylamine and operating at 95° C. The yield was 233 g (54%) of a white crystalline powder soluble in water, hygroscopic, melting at 200°–206° C. (Tottoli), the analysis of which showed a good correspondence with the formula $C_{20}H_{28}N_2O_2S.2HCl$.

EXAMPLE 3

5-[-N-(2,4,6-trimethoxyphenethyl)-N-methyl-2-aminoethyl]-4,5,6,7-tetrahydro-thieno-(3,2-c)-pyridine n=2, $R_1=H$, $R_2=CH_3$, $R_3=2,4,6$-trimethoxy Example 1 was repeated but using N-methyl-2,4,6-trimethoxyphenethylamine instead of 3,4-dimethoxyphenethylamine and operating at 100° C. The yield was 235 g (51%) of a white hygroscopic crystalline product, soluble in water, melting at 192°–194° C. (Tottoli), the analysis of which showed a good correspondence with the formula $C_{21}H_{30}N_2O_3S.2HCl$.

EXAMPLE 4

5-{N-(2,4,6-trimethoxyphenethyl)-N-[4-(3,4-dimethoxyphenyl)-4-cyano-5-methylhexyl]-2-aminoethyl}-4,5,6,7-tetrahydro-thieno-(3,2-c)-pyridine n=2, $R_1=H$, $R_3=2,4,6$-trimethoxy, $R_2=4$-(3,4-dimethoxyphenyl)-4-cyano-5-methylhexyl Example 1 was repeated but using N-[4-(3,4-dimethoxyphenyl)-4-cyano-5-methylhexyl]-2,4,6-trimethoxyphenethylamine instead of 3,4-dimethoxyphenethylamine and operating at 90° C. The yield was 268 g (38%) of a white powder soluble in water, melting at 166°–170° C. (Tottoli), the analysis of which showed a very good correspondence with the formula $C_{36}H_{49}N_3O_5.2HCl$.

EXAMPLE 5

4-(3,4-dimethoxyphenyl)-5-[N-(3,4-dimethoxyphenethyl)-N-methyl-2-aminoethyl]-4,5,6,7-tetrahydro-thieno-(3,2-c)-pyridine $n=2$, $R_1=3,4$-dimethoxyphenyl, $R_2=CH_3$, $R_3=3,4$-dimethoxy Example 2 was repeated but using 4-(3,4-dimethoxyphenyl)-5-(2-chloroethyl)-4,5,6,7-tetrahydro-thieno-(3,2-c)-pyridine instead of 5-(2-chloroethyl)-4,5,6,7-tetrahydro-thieno-(3,2-c)-pyridine and operating at 105° C. The yield was 203 g (41%) of a cream white powder, insoluble in water, melting at 71° C. (Tottoli), the analysis of which showed a good correspondence with the formula $C_{28}H_{36}N_2O_4S$.

EXAMPLE 6

4-(3,4-dimethoxyphenyl)-5-[N-(2,4,6-trimethoxyphenethyl)-2-aminoethyl]-4,5,6,7-tetrahydro-thieno-(3,2-c)-pyridine $n=2$, $R_1=3,4$-dimethoxyphenyl, $R_2=H$, $R_3=2,4,6$-trimethoxy Example 5 was repeated but using 2,4,6-trimethoxyphenethylamine instead of N-methyl-3,4-dimethoxyphenethylamine and operating at 110° C. The yield was 240 g (47%) of a pale yellow powder, soluble in water, melting at 150° C. (Tottoli), the analysis of which showed a perfect correspondence with the formula $C_{28}H_{36}N_2O_5S.2HCl.H_2O$.

EXAMPLE 7

4-(3,4-dimethoxyphenyl)-5-[N-(3,4,5-trimethoxyphenethyl)-2-aminoethyl]-4,5,6,7-tetrahydro-thieno-(3,2-c)-pyridine $n=2$, $R_1=3,4$-dimethoxyphenyl, $R_2=H$, $R_3=3,4,5$-trimethoxy Example 5 was repeated but using 3,4,5-trimethoxyphenethylamine instead of N-methyl-3,4-dimethoxyphenethylamine and operating at 110° C. The yield was 265 g (52%) of a pale yellow powder, soluble in water, melting at 156° C. (Tottoli), the analysis of which showed an excellent correspondence with the formula $C_{28}H_{36}N_2O_5S.2HCl.H_2O$.

EXAMPLE 8

5-[N-(3,4-dimethoxyphenethyl)-N-methyl-3-aminopropyl]-4,5,6,7-tetrahydro-thieno-(3,2-c)-pyridine $n=3$, $R_1=H$, $R_2=CH_3$, $R_3=3,4$-dimethoxy Example 2 was repeated but starting with 5-(3-chloropropyl)-4,5,6,7-tetrahydro-thieno-(3,2-c)-pyridine instead of 5-(2-chloroethyl)-4,5,6,7-tetrahydro-thieno-(3,2-c)-pyridine and operating at 110° C. The yield was 284 g (64%) of a white crystalline powder soluble in water, melting at 235° C. (Tottoli), with decomposition, the analysis of which showed a good correspondence with the formula $C_{21}H_{30}N_2O_2S.2HCl$.

EXAMPLE 9

4-(3,4-dimethoxyphenyl)-5-[N-(3,4-dimethoxyphenethyl)-3-aminopropyl]-4,5,6,7-tetrahydro-thieno-(3,2-c)-pyridine $n=3$, $R_1=3,4$-dimethoxyphenyl, $R_2=H$, $R_3=3,4$-dimethoxy Example 1 was repeated but using 4-(3,4-dimethoxyphenyl)-5-(3-chloropropyl)-4,5,6,7-tetrahydro-thieno-(3,2-c)-pyridine instead of 5-(2-chloroethyl)-4,5,6,7-tetrahydro-thieno-(3,2-c)-pyridine and operating at 100° C. The yield was 338 g (56%) of a white powder, soluble in water, melting at 192° C. (Tottoli), the analysis of which showed a good correspondence with the formula $C_{28}H_{36}N_2O_4S.2HCl.2H_2O$.

EXAMPLE 10

4-(3,4-dimethoxyphenyl)-5-[N-(3,4-dimethoxyphenethyl)-N-methyl-3-aminopropyl]-4,5,6,7-tetrahydro-thieno-(3,2-c)-pyridine $n=3$, $R_1=3,4$-dimethoxyphenyl, $R_2=CH_3$, $R_3=3,4$-dimethoxy Example 9 was repeated but using N-methyl-3,4-dimethoxy-phenethylamine instead of 3,4-dimethoxy-phenethylamine. The yield was 266 g (46%) of a white hygroscopic product, soluble in water, melting at 135°–140° C. (Tottoli), the analysis of which showed a good correspondence with the formula $C_{29}H_{38}N_2O_4S.2HCl$.

EXAMPLE 11

4-(3,4-dimethoxyphenyl)-5-[N-(2,4,6-trimethoxyphenethyl)-N-methyl-3-aminopropyl]-4,5,6,7-tetrahydro-thieno-(3,2-c)-pyridine $n=3$, $R_1=3,4$-dimethoxyphenyl, $R_2=CH_3$, $R_3=2,4,6$-trimethoxy Example 9 was repeated but using N-methyl-2,4,6-trimethoxyphenethylamine instead of 3,4-dimethoxy-phenethylamine and operating at 90° C. The yield was 408 g (67%) of a white hygroscopic powder, soluble in water, melting at 180°–185° C. (Tottoli), the analysis of which showed a very good correspondence with the formula $C_{30}H_{40}N_2O_5S.2HCl$.

EXAMPLE 12

4-(3,4-dimethoxyphenyl)-5-[N-(2,4,6-trimethoxyphenethyl)-3-aminopropyl]-4,5,6,7-tetrahydro-thieno-(3,2-c)-pyridine $n=3$, $R_1=3,4$-dimethoxyphenyl, $R_2=H$, $R_3=2,4,6$-trimethoxy Example 11 was repeated but using 2,4,6-trimethoxyphenethylamine instead of N-methyl-2,4,6-trimethoxyphenethylamine and operating at 110° C. The yield was 273 g (52%) of a white powder, soluble in water, melting at 180° C. (Tottoli), the analysis of which showed a excellent correspondence with the formula $C_{29}H_{38}N_2O_5S.2HCl.H_2O$.

EXAMPLE 13

4-(3,4-dimethoxyphenyl)-5-[N-(3,4,5-trimethoxyphenethyl)-3-aminopropyl]-4,5,6,7-tetrahydro-thieno-(3,2-c)-pyridine $n=3$, $R_1=3,4$-dimethoxyphenyl, $R_2=H$, $R_3=3,4,5$-trimethoxy Example 12 was repeated but using 3,4,5-trimethoxyphenethylamine instead of 2,4,6-trimethoxyphenethylamine and operating at 110° C. The yield was 289 g (55%) of a white powder, soluble in water, melting at 188° C. (Tottoli), the analysis of which showed a perfect correspondence with the formula $C_{29}H_{38}N_2O_5S.2HCl.H_2O$.

EXAMPLE 14

4-(3,4-dimethoxyphenyl)-5-[N-(3,4,5-trimethoxyphenethyl)-N-methyl-3-aminopropyl]-4,5,6,7-tetrahydrothieno-(3,2-c)-pyridine $n=3$, $R_1=3,4$-dimethoxyphenyl, $R_2=CH_3$, $R_3=3,4,5$-trimethoxy Example 13 was repeated but using N-methyl-3,4,5-trimethoxyphenethylamine instead of 3,4,5-trimethoxyphenethylamine and operating at 100° C. The yield was 409 g (63%) of a white hygroscopic powder, soluble in water, melting at 145° C. (Tottoli), the analysis of which showed an excellent correspondence with the formula $C_{30}H_{40}N_2O_5S.2HCl.H_2O$.

EXAMPLE 15

4-(3,4-dimethoxyphenyl)-5-{N-(3,4-dimethoxyphenethyl)-N-[4-(3,4-dimethoxyphenyl)-4-cyano-5-methylhexyl]-3-aminopropyl}-4,5,6,7-tetrahydro-thieno-(3,2-c)-pyridine $n=3$, $R_1=3,4$-dimethoxyphenyl, $R_3=3,4$-dimethoxy, $R_2=4$-(3,4-dimethoxyphenyl)-4-cyano-5-methylhexyl Example 9 was repeated but using N-[4-(3,4-dimethoxyphenyl)-4-cyano-5-methylhyxyl]-3,4-dimethoxyphenethylamine instead of 3,4-dimethoxyphenethylamine and operating at 92° C. The yield was 545 g (66%) of a white hygroscopic powder, insoluble in water, soluble in dimethylsulphoxide, melting at 148°–149° C. (Tottoli), the analysis of which showed a very good correspondence with the formula $C_{44}H_{57}N_3O_6S.2HCl$.

EXAMPLE 16

5[N-(3,4-dimethoxyphenethyl)-N-methyl-4-aminobutyl]-4,5,6,7-tetrahydro-thieno-(3,2-c)-pyridine $n=4$, $R_1=H$, $R_2=CH_3$, $R_3=3,4$-dimethoxy Example 2 was repeated but using 5-(4-chlorobutyl)-4,5,6,7-tetrahydro-thieno-(3,2-c)-pyridine instead of 5-(2-chloro-ethyl)-4,5,6,7-tetrahydro-thieno-(3,2-c)-pyridine and operating at 100° C. The yield was 192 g (42%) of a white crystalline powder, soluble in water, melting at 187° C. (Tottoli), the analysis of which showed a good correspondence with the formula $C_{22}H_{32}N_2O_2S.2HCl$.

EXAMPLE 17

4-(3,4-dimethoxyphenyl)-5-[N-(3,4-dimethoxyphenethyl)-N-methyl-4-aminobutyl]-4,5,6,7-tetrahydrothieno-(3,2-c)-pyridine $n=4$, $R_1=3,4$-dimethoxyphenyl, $R_2=CH_3$, $R_3=3,4$-dimethoxy Example 2 was repeated but using 4-(3,4-dimethoxyphenyl)-5-(4-chlorobutyl)-4,5,6,7-tetrahydro-thieno-(3,2-c)-pyridine instead of 5-(2-chloroethyl)-4,5,6,7-tetrahydro-thieno-(3,2-c)-pyridine and operating at 125° C. The yield was 304 g (58%) of a white crystalline powder, soluble in water, melting at 173° C. (Tottoli), the analysis of which showed a very good correspondence with the formula $C_{30}H_{40}N_2O_4S.2HCl$.

EXAMPLE 18

5-N-{2,4,6-trimethoxyphenethyl)-N-[4-(3,4-dimethoxyphenyl)-4-cyano-5-methylhexyl]-5-aminopentyl}-4,5,6,7-tetrahydro-thieno-(3,2-c)-pyridine $n=5$, $R_1=H$, $R_3=2,4,6$-trimethoxy, $R_2=4$-(3,4-dimethoxyphenyl)-4-cyano-5-methylhexyl Example 4 was repeated but using 5-(5-chloropentyl)-4,5,6,7-tetrahydro-thieno-(3,2-c)-pyridine instead of 5-(2-chloroethyl)-4,5,6,7-tetrahydro-thieno-(3,2-c)-pyridine and operating at 130° C. The yield was 386 g (54%) of a white crystalline powder, slightly soluble in water, melting at 204°–207° C. (Tottoli), the analysis of which showed a very good correspondence with the formula $C_{39}H_{55}N_3O_5.2HCl$.

EXAMPLE 19

4-(3,4-dimethoxyphenyl)-5-[N-(3,4-dimethoxyphenethyl)-N-methyl-5-aminopentyl]-4,5,6,7-tetrahydrothieno-(3,2-c)-pyridine $n=5$, $R_1=3,4$-dimethoxyphenyl, $R_2=CH_3$, $R_3=3,4$-dimethoxy Example 17 was repeated but using 4-(3,4-dimethoxyphenyl)-5-(5-chloropentyl)-4,5,6,7-tetrahydro-thieno-(3,2-c)-pyridine instead of 4-(3,4-dimethoxyphenyl)-5-(4-chlorobutyl)-4,5,6,7-tetrahydro-thieno-(3,2-c)-pyridine and at 120° C. The yield was 264 g (49%) of a white powder, soluble in water, melting at 159°–163° C. (Tottoli), the analysis of which showed a good correspondence with the formula $C_{31}H_{42}N_2O_4S$.

EXAMPLE 20

4-(3,4-dimethoxyphenyl)-5-[N-(2,4,6-trimethoxyphenethyl)-N-methyl-5-aminopentyl]-4,5,6,7-tetrahydrothieno-(3,2-c)-pyridine $n=5$, $R_1=3,4$-dimethoxyphenyl, $R_2=CH_3$, $R_3=2,4,6$-trimethoxy Example 19 was repeated but using N-methyl-2,4,6-trimethoxyphenethylamine instead of N-methyl-3,4-dimethoxyphenethylamine and operating at 120° C. The yield was 318 g (56%) of a white hygroscopic crystalline powder, soluble in water, melting at 193°–197° C. (Tottoli), the analysis of which showed a very good correspondence with the formula $C_{32}H_{44}N_2O_5S.2HCl$.

TOXICITY

The toxicity of the compounds of the invention has been determined per os and I.P. None of them presented a $DL_{50}$ inferior to 750 mg/kg per os or 160 mg/kg I.P.

PHARMACOLOGY

The interest of the compounds of the invention was evidenced by the following pharmacological tests.

1. Anti-thrombotic Acitivity on Rat Carotid Artery

Female CD Sprague-Dawley rats (190–235 g) were anaesthetised with urethane (5 ml/kg I.P. of a 25% solution in 0.9% saline). The left carotid artery was exposed for a length of approximately 2 cm and placed over shielded stainless steel electrodes spaced 0.5 cm apart. A thermistor for recording arterial surface temperature was placed around the artery 1 cm distal the electrodes; the thermistor was connected to a recorder.

A current of 1.5 mA was passed through the arterial electrodes for two minutes using a stimulator linked to a constant current unit. The time from commencing electrical stimulation to a rapid and marked fall in the surface temperature of the artery was taken as the time to thrombus formation. If appropriate, the recording could be continued for up to 45 minutes after electrical stimulation.

Batches of each 10 animals received test compounds (50 mg/kg, per os), reference compounds: acetylsalicylic acid or ticlopidine, at 100 mg/kg or vehicle orally at a dose volume 10 ml/kg, 50 minutes prior to induction of anaesthesia.

In this test, the compounds of examples 2, 5, 9, 10, 11 and 20 were used. They led to a significant increase in time to thrombus formation (from 37 to 87%).

2. Action on Cardiovascular Hemodynamics on Anaesthetised Dog

This experiment was conducted on compounds of examples 1 to 20 included and showed, when administered I.V. at 2.5 mg/kg, the following variations.
Blood pressure (systolic): decrease from 10.5 to 28%
Blood pressure (diastolic): decrease from 22 to 52%
Cardiac rythm: decrease from 0 to 14%
Coronary flow: increase from 60 to 170%
Vertebral flow: increase from 135 to 285%
Femoral flow: increase from 37 to 85%.

3. In Vitro Aggregation of Human Platelets by Arachidonic Acid

In this experiment, the compounds of the invention presented a marked action against human platelets aggregation.

4. Calcium Antagonist Activity

This activity was demonstrated by the isolated rabbit aorta test (relaxation after contraction induced by KCl). The compounds showed an action at doses of about $10^{-6}$M. Although this activity is less favourable than that one of verapamil, this side action is complementary to the action evidenced by the preceding tests.

PRESENTATION—POSOLOGY

In human therapy, unit doses contain 0.1 to 0.25 g of active ingredient associated with appropriate diluent or carrier. For I.V. administration, phials containing 0.1 g of the selected derivative are used; daily posology 1 to 3 phials. For oral administration, tablets, gelatine capsules, for instance, contain 0.25 g; daily posology 1 to 4 dose units.

I claim:

1. A derivative of 5-(ω-phenethylamino-alkyl)-4,5,6,7-tetrahydro-thieno-(3,2-c)-pyridine of the formula

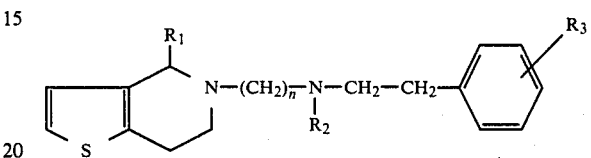

wherein n is an integer of from 2 to 5, $R_1$ represents a hydrogen atom or a 3,4-dimethoxyphenyl group, $R_2$ represents a hydrogen atom, an alkyl group having up to 4 carbon atoms or a 4-cyano-4-(3,4-dimethoxyphenyl)-5-methylhexyl group and $R_3$ represents two or three methoxy groups; and therapeutically acceptable salts thereof.

2. An anti-thrombotic therapeutic composition of matter containing, as an active ingredient therein, an anti-thrombotically effective amount of a compound according to claim 1 in admixture with a therapeutically acceptable diluent or carrier.

* * * * *